United States Patent
Stokes et al.

(10) Patent No.: US 6,670,820 B2
(45) Date of Patent: Dec. 30, 2003

(54) METHOD AND APPARATUS FOR EVALUATING ELECTROLUMINESCENCE PROPERTIES OF SEMICONDUCTOR MATERIALS AND DEVICES

(75) Inventors: Edward Brittain Stokes, Schenectady, NY (US); Robert F. Karlicek, Jr., Twinsburg, OH (US)

(73) Assignee: General Electric Company, Schenectady, NY (US)

( * ) Notice: Subject to any disclaimer, the term of this patent is extended or adjusted under 35 U.S.C. 154(b) by 84 days.

(21) Appl. No.: 09/683,421

(22) Filed: Dec. 27, 2001

(65) Prior Publication Data

US 2003/0122561 A1 Jul. 3, 2003

(51) Int. Cl.[7] .................. G01R 31/26; G01R 31/302; G01N 21/00
(52) U.S. Cl. .................. 324/767; 324/752; 356/237.1
(58) Field of Search .................. 324/767, 753, 324/765, 752, 96; 356/237.1

(56) References Cited

U.S. PATENT DOCUMENTS 4,968,932 A * 11/1990 Baba et al. .................. 324/767

* cited by examiner

*Primary Examiner*—John E. Chapman
*Assistant Examiner*—James Kerveros
(74) *Attorney, Agent, or Firm*—Fay, Sharpe, Fagan, Minnich & McKee, LLP

(57) ABSTRACT

An apparatus for evaluating an associated semiconductor sample having two electrically distinct regions with a junction region disposed therebetween includes a laser for injecting carriers into a sample region, an electrical bias for impressing electrical fields on the sample, and a detector for detecting luminescence. A second laser is provided for injecting carriers into a second sample region opposite the first region. A method includes the steps of: optically generating carriers in a region, generating a drift field in the region that effectuates carrier drift toward the junction, and measuring the optical radiation generated by carrier recombination in the junction region. Preferably, the method also includes optically generating carriers in a second region and generating a drift field in the second region that effectuates carrier drift toward the junction. Typically, the two drift fields are generated together by applying voltage between the two regions.

17 Claims, 3 Drawing Sheets

METHOD AND APPARATUS FOR EVALUATING ELECTROLUMINESCENCE PROPERTIES OF SEMICONDUCTOR MATERIALS AND DEVICES

BACKGROUND OF INVENTION

The invention relates to semiconductor materials and devices characterization or evaluation, and more particularly to the electrical and optical characterization of light emitting diode (LED) device structures. The invention will be described with particular reference to the characterization of quantum well-based LED structures. However, the invention is not so limited, but will also find application in optical and optoelectronic evaluation of p/n junctions, semiconductor laser structures, and the like.

The prior art discloses semiconductor characterization using a very broad range of experimental techniques. Semiconductor materials and devices are commonly characterized or evaluated using x-ray diffractometry, photoluminescence, cathodoluminescence, and electroluminescence, among many other techniques. In the case of optoelectronic devices which convert electrical energy to optical energy and/or vise versa, methods which excite luminescence in the material are particularly useful. In photoluminescence, excess carriers (excess electron-hole pairs) are photoexcited by exposure to a sufficiently intense light source, and the luminescence emitted as these photoexcited carriers recombine is measured. The luminescence can be measured spectroscopically and/or as a function of time after the light source is turned off. Cathodoluminescence is similar to photoluminescence except that the excess carriers are generated by exposure to an electron beam rather than by exposure to light.

For evaluating a light emitting diode (LED) device structure, the electroluminescence behavior is of greatest interest, as the finished LED device functions through electroluminescence. Electroluminescence is similar to photoluminescence and cathodoluminescence, except that in electroluminescence the excess carriers are electrically injected. In the case of an LED, the electrical injection of carriers into the optically active p/n junction region is achieved by forward biasing the p/n junction. However, electroluminescence is not equivalent to photoluminescence, because the electroluminescence behavior of a sample is determined by a number of factors, such as the optical properties of the optically active layers, the electrical transport properties (e.g., conductivity) of the p-type and n-type regions, and the properties of the electrical contacts through which the electrical biasing is applied. Some of these factors, particularly those relating to transport, can produce different effects on the electroluminescence versus the photoluminescence. It is to be appreciated that in photoluminescence, both the excess conduction electrons and the excess holes are typically injected into the same side of the junction, whereas in electroluminescence the injection of electrons and holes are on opposite sides of the junction.

An important class of LED's are epitaxially grown double heterostructure-based LED's (DH-LED's). In these devices, the simple doping junction of the standard p/n diode LED is replaced by an active region containing luminescent material, and with an energy gap less than that of the surrounding p and n type materials. The active region is preferably sandwiched between the p-type and n-type regions of the DH-LED. Light emission in a DH-LED is through the radiative recombination of electrically injected excess carriers inside the active layer. The active layer of a DH-LED defines a potential well. If the dimension of the active layer is less than about 10 nm, then the double heterostructure is called a quantum well. Multiple quantum wells can exist in the active layer of a heterostructure LED.

The active region of a DH-LED serves, in addition to physically hosting the luminescent material, as a carrier confinement region that confines carriers inside the active layer or quantum wells. If an electron-hole pair exists inside a potential well, the likelihood of recombination increases as the width of the well decreases. This is simply because the electron is physically closer to the hole in a narrow potential well than in a wider potential well.

The electroluminescence of DH-LED's and quantum well-based LED's is further complicated by the additional structural complexity. The electroluminescence can be affected by factors such as the effectiveness of the carrier confinement, interfacial defects, impurities at the quantum well boundaries or inside the quantum wells, the relative confinement of conduction electrons versus holes (typically determined by the conduction band and valence band offsets at the interface between the quantum well and the barrier material), crystalline quality of the quantum wells, atomic interdiffusion at the quantum well interfaces, and the like. It will again be appreciated that these effects can be different for electroluminescence versus photoluminescence.

Commercial LED wafers are typically tested at the wafer level using photoluminescence. However, it is generally known to the art that high photoluminescence efficiency is a necessary but not a sufficient test of an LED wafer. A wafer that exhibits poor active layer photoluminescence properties will usually also exhibit poor electroluminescence behavior, translating into poor LED's fabricated therefrom. However, a wafer with high photoluminescence efficiency may or may not produce high electroluminescence efficiency and hence good LED's, because of differences between the electroluminescence and photoluminescence processes as discussed above. Thus, there remains an unfulfilled need for improved screening of LED wafers at the wafer level.

The prior art also does not teach effective means for separating out the various components of the electroluminescence signal. Poor electroluminescence or LED behavior can result from failure at any layer of the LED structure, or from problems introduced during LED fabrication. The prior art teaches generating a matrix of varying sample growth conditions and fabrication steps and analyzing the matrix, e.g. by fabricating LED's therefrom, in the hope of correlating the matrix parameters with changes in the LED behavior or the electroluminescence. This approach has several disadvantages. First, it is expensive in terms of personnel time, equipment load, and source materials. Second, it is highly subjective. Misleading results can easily be obtained if elements of the sample matrix include unknown variations, e.g. differences in doping level between samples for a layer which has the same nominal doping level for all the samples of the matrix. Even if an unintended matrix variation is recognized, e.g. through doping concentration measurements, it still can be difficult or even impossible to correct the data therefor.

In view of these disadvantages, it would be useful to have an improved characterization method that preferably is performed at the wafer level and more closely resembles the physical mechanisms of electroluminescence and LED operation, and that has the ability to independently evaluate for a single sample the relative contributions or effects on the electroluminescence characteristics of the various sample regions such as the active region including the quantum well or wells, the p-type material region, the n-type material region, and the electrical contacts.

The present invention contemplates such an improved characterization or evaluation method and apparatus.

SUMMARY OF INVENTION

In accordance with one aspect of the present invention, an apparatus for evaluating an associated semiconductor sample is disclosed. The associated sample has a first electrically distinct region and a second electrically distinct region, and further has a junction region disposed therebetween. The evaluation apparatus includes a stage for mounting the semiconductor sample. A first laser has a wavelength tuned to photogenerate carriers in the first electrically distinct region. An electrical biasing means is provided for impressing an electrical field whereby at least some photoexcited carriers are influenced to drift toward the junction region. The photoexcited carriers are holes from the p-side and electrons from the n-side. In this manner, instead of injecting electron-hole pairs from one side through thermal diffusion, electrons and holes are injected from different sides as they would be in an actual LED. An optical detector is provided, whereby luminescence generated by recombination of the photoexcited carriers in the junction region is detected.

Preferably, the apparatus includes a translation means for relatively translating the laser and the sample whereby the laser beam is scanned across the sample. A second laser is preferably disposed on the opposite side of the sample with respect to the first laser. The second laser has a wavelength tuned to photogenerate carriers into the second electrically distinct region. Preferably, the first laser has a wavelength tuned to a first energy approximately corresponding to the energy band gap of a material comprising the first electrically distinct region, while the second laser has a wavelength tuned to a second energy approximately corresponding to the energy band gap of a material comprising the second electrically distinct region. Optionally, the two wavelengths can be the same, i.e. the same laser beam is split to serve as both the first laser and the second laser.

In one application, the associated sample has at least one potential well in the junction region. The optical detector preferably has a detection wavelength range which essentially includes the active layer luminescence. In a more specific application, the first region of the associated sample includes n-type gallium nitride, the second region of the associated sample includes p-type gallium nitride, and the active layer of the associated sample includes an alloy of indium gallium nitride. In this case, the first laser and the second laser preferably have wavelengths less than 365 nm to provide adequate absorption by the semiconductor. Preferably, at least one of the group including the first laser and the second laser is a tunable wavelength laser.

In accordance with another aspect of the present invention, a method for characterizing an associated semiconductor sample is disclosed. The associated sample has a first electrically distinct region and a second electrically distinct region, and further has a junction region disposed therebetween. The characterization method includes the steps of optically generating carriers in the first electrically distinct region, generating an externally applied drift field in the first region that effectuates a drifting of the optically generated carriers in the first electrically distinct region toward the junction region, and measuring the optical radiation generated by radiative recombination of the optically generated carriers in the junction region.

Preferably, the characterization method also includes optically generating carriers in the second electrically distinct region, and generating an externally applied drift field in the second region that effectuates a drifting of the optically generated carriers in the second electrically distinct region toward the junction region. Typically, the step of generating an externally applied drift field in the first region and the step of generating an externally applied drift field in the second region are performed together by applying a voltage between an electric contact that electrically contacts the first electrically distinct region and an electric contact that electrically contacts the second electrically distinct region.

In the step of generating an externally applied drift field in the first region, an electric drift field described by a field vector E is generated. Preferably, in the step of optically generating carriers in the first electrically distinct region, the optically generated carriers are substantially generated within a distance $d=\mu\tau|E|$ of the junction region, where $\mu$ is the drift mobility of the optically generated carriers in the first material, and $\tau$ is the lifetime of the optically generated carriers in the first material. Under these conditions, the fraction of the optically generated carriers which enter the junction region is approximately 1/e.

The method preferably further includes estimating quantitatively the volume recombination rate in the junction region based on the step of measuring the optical radiation generated by radiative recombination of the optically generated carriers in the junction region; estimating quantitatively the volume density of optically generated carriers in the first electrically distinct region; and estimating quantitatively the electroluminescence efficiency based upon the volume recombination rate and the volume density of optically generated carriers.

In the above method, the magnitude of the drift field produced in the step of generating an externally applied drift field in the first region is preferably sufficiently low such that the number of carriers electrically generated is negligible compared to the optically generated carriers.

In accordance with yet another aspect of the present invention, A method for characterizing a light emitting diode (LED) structure sample is disclosed. The sample has an n-type region and a p-type region with a junction region disposed therebetween. Carriers are optically generated in the n-type region by light impingement thereon. Carriers are optically generated in the p-type region by light impingement thereon. The optical radiation generated by radiative recombination of the optically generated carriers in the junction region is measured.

Preferably, the method further includes electrically biasing the junction and to effectuate a drifting of the optically generated carriers toward the junction region.

Preferably, the method further includes optically chopping the impinging light with an optical chopper, detecting the optical radiation with an optical detector, and measuring the optical detector signal at the optical chopping frequency using a lock-in amplifier that is in operative communication with the optical chopper and the optical detector.

Preferably, the method further includes repeating the generating, biasing, and measuring steps at a plurality of wavelengths of the at least one optical source, and estimating transport properties of the at least one region therefrom.

Preferably, the method further includes repeating the generating, biasing, and measuring steps at a plurality of intensities of the at least one optical source, and estimating the effects of high injection levels from the measuring.

One advantage of the present invention is that it permits separately probing the effects of transport in the p-type and n-type regions, artifacts due to the electrical contacts, and properties intrinsic to the active region.

Another advantage of the present invention is that it permits spatial profiling of the LED heterostructure across the wafer.

Another advantage of the present invention is that it permits depth-dependent profiling into both the n-side and the p-side of the LED structure.

Yet another advantage of the present invention is that it facilitates photoexcited electroluminescence whereby simultaneous excitation from the front and the rear of the wafer is performed.

Still yet another advantage of the present invention is that it provides a wafer level characterization method that is closer to the physical behavior of an operating LED versus prior art wafer level characterization methods.

Still further advantages and benefits of the present invention will become apparent to those of ordinary skill in the art upon reading and understanding the following detailed description.

BRIEF DESCRIPTION OF DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION

Figure 1:
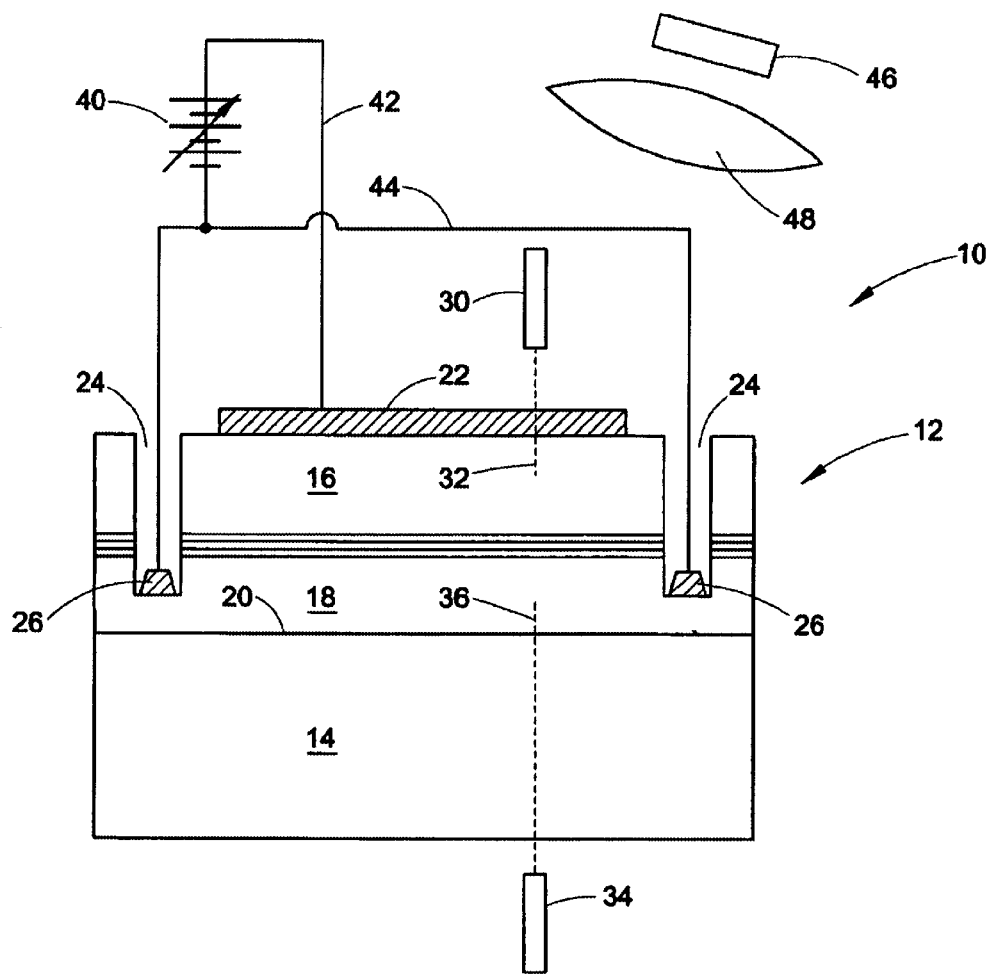
FIG. 1 is a drawing of an experimental apparatus according to one embodiment of the invention.

With reference to FIG. 1, an experimental apparatus 10 is described in accordance with one embodiment of the invention. The experimental apparatus 10 operates upon an associated LED sample 12. The associated sample 12 includes a substrate 14 and typically a plurality of semiconductor layers 16, 18, 20 usually grown epitaxially thereon. In FIG. 1, an exemplary gallium nitride (GaN) based LED sample 12 is shown, which includes a sapphire substrate 14, a p-type GaN region 16 and an n-type GaN region 18. Sandwiched between the p-type GaN region 16 and the n-type GaN region 18 are a plurality of $In_xGa_{1-x}N$ quantum wells 20 which comprise the active region of the LED device. "Quantum wells" are InGaN layers typically around 10 nm thick or less. Although four quantum wells 20 are drawn, it is to be appreciated that GaN QW-LED's with as few as one InGaN layer are feasible, and the layer need not be a quantum well. The $In_xGa_{1-x}N$ layers are alloys of InN and GaN, and the mole fraction of InN in the quantum well or wells, denoted by x in the formula $In_xGa_{1-x}N$, strongly affects the LED emission peak wavelength, through the band gap of the $In_xGa_{1-x}N$ material, and through an incompletely understood mechanism involving physical segregation of InN from GaN in the alloy. Additional layers, such as nucleation buffer layers (not shown) are also optionally incorporated to facilitate the crystal growth or for other reasons related to the design and performance of the LED. Of course, the invention is not limited in application to the exemplary GaN-based LED structure drawn in FIG. 1, but will also find application in the characterization of a wide range of LED structures comprising various materials and various layer combinations, as well as in the characterization of other optoelectronic materials and devices such as semiconductor laser device structures.

With continuing reference to FIG. 1, a p-type electrical contact 22 is formed which contacts the p-type region 16. A series of vias 24 are etched through the p-type region 16 and the quantum wells 20 thereby exposing portions of the n-type region 18, and n-type electrical contacts 26 are formed therein. It will be appreciated that the p-type electrical contact 22 preferably includes a region which is essentially transparent with respect to the photoexcitation light source which will be described next. In the illustrated embodiment of FIG. 1 this transparent area includes the entire contact 22 area. In a preferred embodiment for a group III-nitride LED, a nickel oxide/gold or cobalt oxide/gold contact is used for the p-type contact 22. This contact is preferably formed by depositing 5–10 nm of nickel followed by 5–10 nm of gold and annealing the contact at 450–600° C. for 5 minutes in air. The thickness of the gold is sufficiently thin in the region of photoexcitation light impingement to ensure good transparency. Of course, the described contact is exemplary only, and other transparent contacts may be used instead. The vias 24 and the contacts 22, 26 are preferably formed using standard semiconductor processing techniques well known to those skilled in the art.

It will be appreciated that the fabrication steps just described can be performed at the wafer level in an essentially non-destructive manner. Depending upon the conductivity of the n-type layer or of the underlying substrate, the contact vias are optionally restricted to peripheral areas of the wafer so that the central wafer areas remain undisturbed and available for subsequent commercial LED device fabrication. In one embodiment, the Ni/Au oxidized contact is the first step of the LED fabrication process. In another embodiment, the Ni/Au oxidized contact is selectively removable using standard etching methods that are well known to those of ordinary skill in the art. It will also be appreciated that for conductive substrates such as silicon carbide or gallium nitride, the contact vias 24 are optionally replaced by direct electrical contact to the conductive substrate, further facilitating wafer-level testing.

With continuing reference to FIG. 1, the experimental apparatus 10 includes a first light source 30 which applies a first photoexcitation light 32 to the p-type region 16 through the transparent region of the p-type electrical contact 22. In a preferred embodiment, the first light source 30 is a laser with a well defined lasing wavelength, although lamp systems with appropriate conditioning optics such as wavelength-selective filters can be substituted therefor. Preferably, a second light source 34 applies a second photoexcitation light 36 in the n-type region 18. It will again be appreciated that the second photoexcitation light 36 should pass through the substrate 14 without excessive optical attenuation. In the exemplary case of a sapphire substrate, this transparency condition is met for a preferred wavelength range around approximately 365 nm or shorter (sapphire is transparent down to 200 nm) which is appropriate for photoexcitation of the GaN regions 16, 18, as well as for the wavelength range around approximately 365 nm or longer which is appropriate for photoexcitation of typical $In_xGa_{1-x}N$ quantum wells. For partially opaque substrates, the substrate is optionally thinned in the region of interest to obtain sufficient transparency.

With continuing reference to FIG. 1, the experimental apparatus 10 also includes a biasing means 40 for applying a variable electrical bias to the sample 12. In the apparatus drawn in FIG. 1, the biasing means is a d.c. voltage source 40, such as a battery with a variable resistor, a commercial d.c. power supply, a custom-built power supply, or the like. The biasing means 40 is preferably connected to the p-type contact 22 by wiring 42, and to the n-type contacts by wiring 44. In one embodiment of the invention, the DC bias is applied just below threshold, so that the only spatial region of significant current flow through the active layer is near the photoexcited volume. It will be appreciated that the biasing means can take various other forms.

The experimental apparatus 10 also includes an optical detector 46 which detects luminescence generated by the associated sample 12 under the influence of the experimental apparatus 10. The detector 46 can be a photomultiplier tube, a photodiode, a diode array, or the like, and also preferably includes a light-collecting lens 48, optical fiber coupling (not shown), appropriate drive electronics (not shown), and a dispersive component such as a monochromator, spectrograph, or the like.

Figure 2:
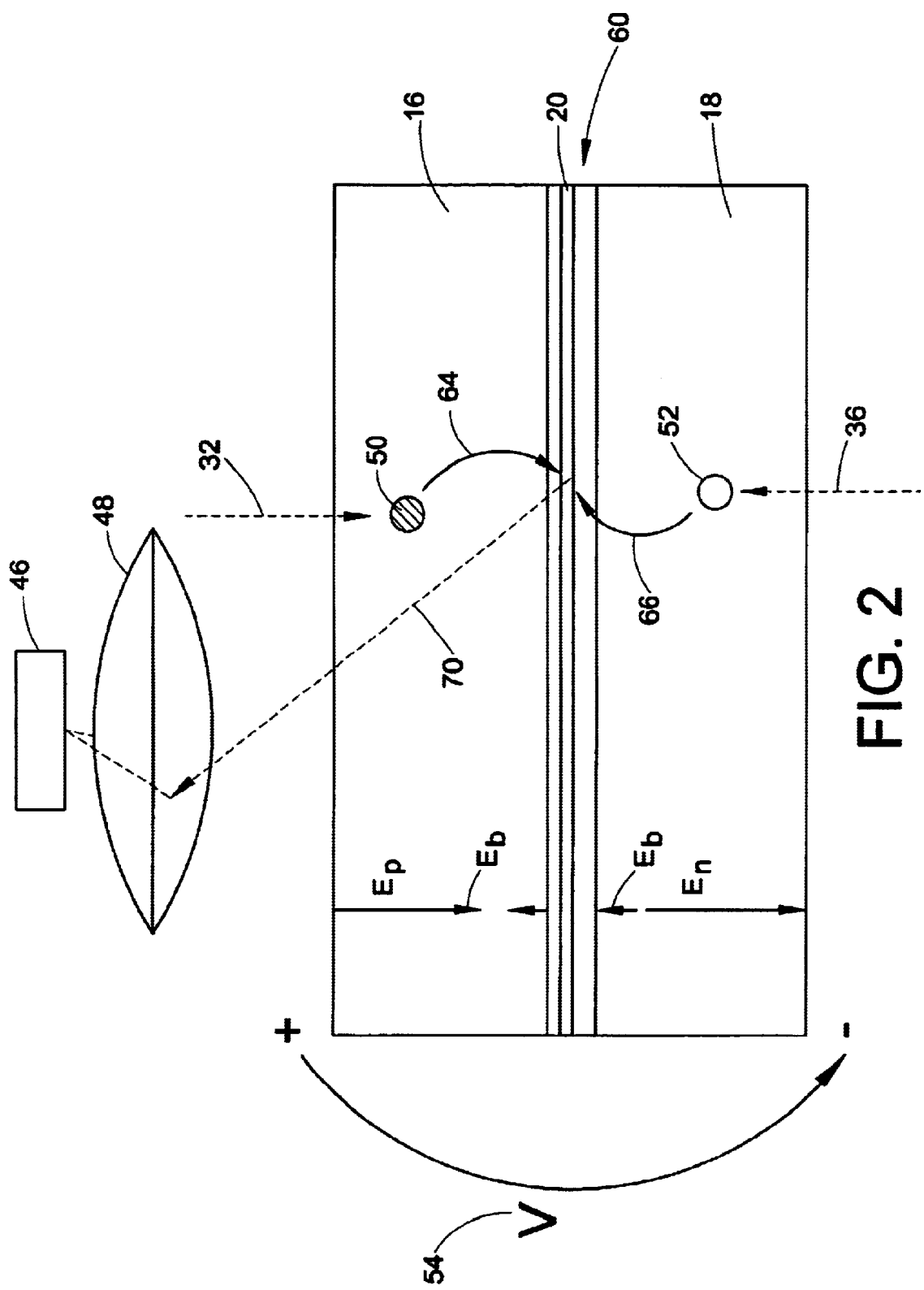
FIG. 2 is a drawing of the physical processes which occur inside the sample during a method carried out in accordance with the apparatus drawn in FIG. 1.

With continuing reference to FIG. 1, and with further reference to FIG. 2, an exemplary method implemented by the experimental apparatus 10 is described. The first photoexcitation light 32 impinges on the p-type region 16. For a properly selected wavelength, the photoexcitation light 32 is absorbed primarily in the p-type region 16. The photon absorption process photogenerates electron-hole pairs. The wavelength is selected to position the photoexcited electron-hole pair distribution essentially within a certain depth range, which is determined by the absorption spectrum of the material or materials comprising the p-type region 16. In the p-type material 16, photoexcited majority carrier holes are represented in FIG. 2 by an exemplary hole 50. Similarly, the second photoexcitation light 36 having a wavelength selected to be absorbed in the n-type region 18 will generate electron-hole pairs therein, and the photoexcited electrons are represented in FIG. 2 by an exemplary electron 52. It will be appreciated that this excess carrier injection arrangement differs fundamentally from that of conventional photoluminescence, because in conventional photoluminescence one or the other of the light sources is absent, and so transport in one of the cladding layers is not investigated. The optical injection arrangement shown in FIG. 2 more closely resembles the actual operation of the final LED device.

The biasing means 40 generates a voltage 54 across the sample as shown in FIG. 2. The voltage 54 generates electric fields $E_p$, $E_n$ in the bulk p-type 16 and n-type 18 regions, respectively. In FIG. 2, the LED 12 is placed in forward bias corresponding to the typical biasing polarity of an operational LED. However, methods employing the apparatus 10 in which a reverse bias is applied are also contemplated. It will be appreciated that the polarity of the forward bias voltage 54 and of the corresponding impressed electric fields $E_p$, $E_n$ are such that both the photoinjected holes 50 and the photoinjected electrons 52 are influenced to move toward the junction region 60. Within the junction region, an active layer or one or more quantum wells 20 exist. In FIG. 2, a single quantum well 20 is shown for simplicity. The electron and the hole drift under the influence of the applied voltage 54 along paths 64 and 66 for the hole 50 and the electron 52, respectively. The holes 50 and the electron 52 preferably recombine inside the quantum well and emit a photon represented by a ray 70 which contributes to the sample luminescence collected by the collecting lens 48 and measured by the detector 46.

For a sufficiently high applied voltage the electrically injected carriers in an LED will be more numerous than the photoexcited carriers. Here, however, lower voltages 54 are typically applied, so that the applied voltage 54 is merely influencing the photoexcited carriers to move toward the junction. Lower applied voltages typically reduce non-ohmic contact behavior so that the sample response is more characteristic of the semiconductor layers rather than the contacts. The local threshold voltage in an LED wafer is depressed by the presence of photoexcited carriers, particularly in the p-type material. In one embodiment, the forward bias 54 is set just below threshold, so that the luminescence will be generated predominantly in the photoexcited volume.

In one exemplary embodiment in which the associated LED structure is a simple p/n homojunction without quantum wells (sample not shown), an appropriate electric field magnitude can be estimated based on the drift velocity $v=\mu|E|$ where $\mu$ is the drift mobility of the optically generated carriers in the material and $|E|$ is the magnitude of the electric field impressed by the voltage 54, e.g. the field $E_p$ or the field $E_n$. The average distance a carrier moves before recombining is $d=v\tau=\tau\mu|E|$ where $\tau$ is the carrier lifetime in the material. Based upon such transport estimates, the fraction of photoinjected carriers expected to reach the junction region is estimated. Furthermore, the volume density of photoinjected carriers is obtained from the light intensity and the absorption characteristics of the material. The volume (or areal) recombination rate in the junction region is estimated from the luminescence intensity measured by the detector 46 along with geometrical factors. The electroluminescence efficiency is obtained from the volume (or areal) recombination rate and the volume density of optically generated carriers, taking into account the fraction of carriers which reach the junction region.

The above-described homojunction LED calculations are exemplary only. Particularly in more complex heterojunction-based LED's such as the exemplary GaN LED 12 of FIG. 1, the effectiveness of the bias voltage 54 in driving carriers into the active region (e.g., the p-type region 16 or the n-type region 18) will depend upon many factors, such as contact resistance, doping levels, potential barriers in the active region, and et cetera. In FIG. 2, exemplary potential barriers $E_b$ can impede injection of carriers into the quantum well 20. Even in the case of a homojunction LED complexities can arise due to impurities, non-uniform dopant distributions, and the like. Because of the complexity of a typical LED samples, quantitative calculations are often impractical in practice. However, by varying selected operational parameters of the apparatus 10 while holding other operational parameters constant, as described next, the individual electroluminescence contributions of the various structural regions of the sample can be separately and independently examined.

With continuing reference to FIGS. 1 and 2, a typical evaluation or characterization of an associated sample such as the exemplary GaN LED 12 using the exemplary method and apparatus of FIGS. 1 and 2 is described. For some measurements, the first and second light sources 30, 34 of the apparatus 10 are preferably wavelength-tunable sources. By obtaining data for several wavelengths of the first light source 30 while holding the other operational parameters of the apparatus 10 constant (e.g., constant electrical bias 54, constant intensity and wavelength for the second light source 34), the carrier injection from the p-type region 16 is investigated. Varying the wavelength varies the depth of the photoinjected carriers, so that the electroluminescence variation with the wavelength of the first light source 30 correlates with the carrier transport properties of the p-type region 16. Such measurements also can provide information about potential barriers $E_b$ which may be impeding carrier injection from the p-type region 16 into the junction region 60. In an analogous manner, varying the second light source 34 while holding the other operational parameters constant probes carrier injection from the n-type region 18.

In another characterization aspect, by increasing the intensity of light sources 30, 34 together or independently, the effects of high injection levels into one or both regions 16, 18 is probed essentially independently from contact behavior artifacts which are usually produced at high current levels. In yet another variation, keeping the light sources constant while varying the applied voltage 54 probes factors whose effect on the electroluminescence correlate with high bias voltage 54. For example, the effects of high contact resistances at the contacts 22, 26 can be investigated in this manner.

For sufficiently long wavelengths, the absorption typically takes place predominantly inside the quantum wells. Considering the exemplary GaN QW-LED 12, the p-type and n-type regions 16, 18 are comprised of GaN while the quantum wells are comprised of $In_xGa_{1-x}N$ material which has a lower-band gap. Under selected long wavelength conditions, absorption occurs primarily in the $In_xGa_{1-x}N$ and so transport through the p-type and n-type regions 16, 18 is essentially irrelevant. The luminescence properties of the active region as a function of applied electrical bias can thus be evaluated directly and independently from the cladding regions 16, 18.

In the apparatus 10, the associated sample 12 is preferably mounted on a translation stage (not shown) whereby the sample 12 is moved laterally with respect to the light sources 30, 34. In this way, lateral inhomogeneities can be probed. Lateral translation is often useful for detecting variations in quantum well thickness across the wafer, for example. Material damage near an alloyed contact can also be evaluated by scanning the injection region toward the contact.

In the apparatus embodiment of FIG. 7, two independent light sources 30, 34 are used to inject carriers into the p-type region 16 and the n-type region 78, respectively. This approach enables the use of different wavelengths for exciting the two sides of the junction. The two excitation beams optionally have different coordinates in the horizontal plane so as to probe lateral diffusion and drift effects; also the two excitation beams are optionally pulsed, with pulse width short compared to carrier lifetime so as to probe temporal drift, diffusion, and recombination effects; furthermore the pulses need not be coincident, so as to independently probe temporal drift, diffusion, and recombination effects in the n and p type material. However, in many cases the two sides are comprised of the same material, e.g. GaN. For such samples, separate wavelength adjustment capability for each of the two sides of the junction may not be particularly advantageous.

Figure 3:
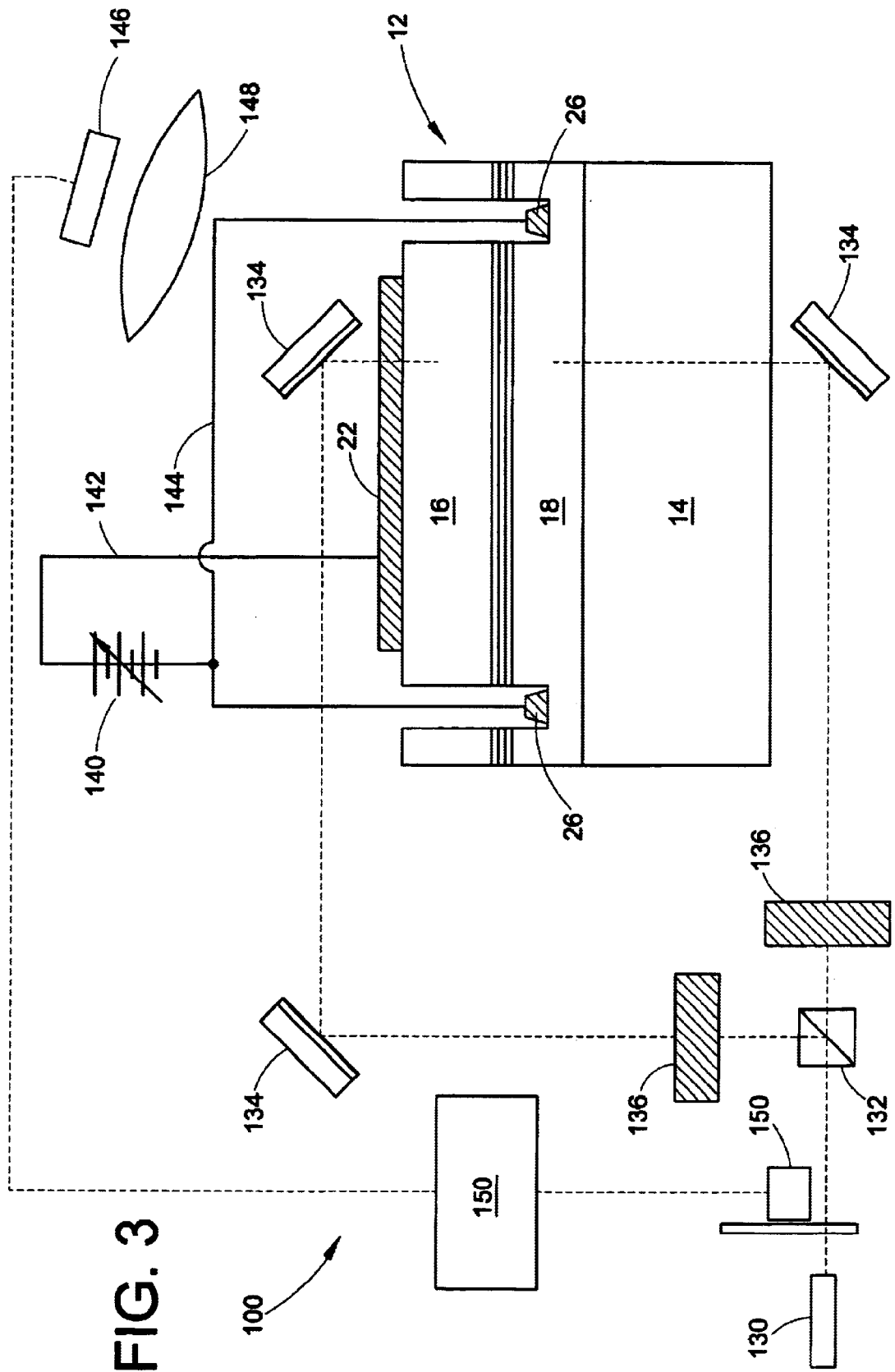
FIG. 3 is a drawing of an experimental apparatus according to another embodiment of the invention.

With reference to FIG. 3, a second apparatus embodiment 100 of the invention is described. The embodiment is shown acting on the same exemplary GaN-based sample 12 as is shown in FIG. 7. The biasing arrangement, comprising variable biasing means 140 and wiring 742, 144 is preferably essentially unchanged from the embodiment of FIG. 1. However, the two light sources 30, 34 of the embodiment of FIG. 1 are replaced in the embodiment of FIG. 3 by a single light source 130 with a beam splitter 132, several mirrors 134, and two variable intensity attenuators 136 which can take the form of filter wheels, removably insertable neutral density filters, shutters, or the like. The single light source 130 is preferably an adjustable wavelength light source.

The light detection is preferably by an optical detector 146 and a light collecting lens 148, both of which are similar to the corresponding components of the first apparatus of FIG. 1. However, because a single light source is used, the apparatus of FIG. 3 optionally includes a lock-in detection sub-system including an optical chopper 150 and a lock-in amplifier 152 in operative communication with the optical chopper 150 and the optical detector 146. As is known to those skilled in the art, use of lock-in detection greatly increases the signal-to-noise ratio of the detected luminescence signal. Of course, other signal detection sub-systems can be substituted therefor.

The methods described with respect to the apparatus of FIG. 1 are also generally compatible with the apparatus of FIG. 3. However, with the apparatus of FIG. 3 the wavelength of light impinging on the p-type region 16 and the n-type region 18 cannot be independently varied. The relative light intensities are, however, independently variable through the two variable attenuators 136, and so the magnitude of the carrier injection into the two regions 16, 18 can be independently controlled.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. An apparatus for evaluating a semiconductor sample, said sample having a first electrically distinct region and a second electrically distinct region, and having a junction region disposed therebetween, the evaluation apparatus comprising:

a stage for mounting the semiconductor sample;

a first laser having a wavelength tuned to photogenerate carriers in the first electrically distinct region;

a second laser disposed on the opposite side of the sample with respect to the first laser and having a wavelength tuned to photogenerate carriers in the second electrically distinct region;

an electrical biasing means for impressing an electrical field whereby at least some of the photoexcited carriers generated by the first and second lasers are influenced to drift toward the junction region; and an optical detector whereby luminescence generated by recombination of the photoexcited carriers in the junction region is detected.

2. The apparatus as set forth in claim 1, further comprising:

a translation means for relatively translating the laser and the sample whereby the laser beam is scanned across the sample.

3. The apparatus as set forth in claim 1, wherein:

the first laser has a wavelength tuned to a first energy approximately corresponding to the energy band gap of a material comprising the first electrically distinct region; and the second laser has a wavelength tuned to a second energy approximately corresponding to the energy band gap of a material comprising the second electrically distinct region.

4. A The apparatus as set forth in claim 3, wherein:

the junction region of the associated sample includes at least one quantum well; and the optical detector has a detection wavelength range which essentially includes the quantum well luminescence.

5. The apparatus as set forth in claim 1, wherein:
at least one of the first laser and the second laser is a tunable wavelength laser.

6. An apparatus for evaluating a semiconductor sample, said sample having a first electrically distinct region and a second electrically distinct region, and having a junction region disposed therebetween that includes at least one quantum well, the evaluation apparatus comprising:
a first laser having a wavelength tuned to photogenerate carriers in the first electrically distinct region;
a second laser disposed on the opposite side of the sample with respect to the first laser and having a wavelength tuned to photogenerate carriers in the second electrically distinct region;
an electrical biasing means for impressing an electrical field whereby at least some of the photoexcited carriers are influenced to drift toward the junction region; and
an optical detector having a detection wavelength range which includes the quantum well luminescence whereby luminescence generated by recombination of the photoexcited carriers in the junction region is detected; wherein
the first laser has a wavelength tuned to a first energy approximately corresponding to the energy band gap of a material comprising the first electrically distinct region;
the second laser has a wavelength tuned to a second energy approximately corresponding to the energy band gap of a material comprising the second electrically distinct region;
the first region of the associated sample includes n-type $In_{x1}Al_{y1}Ga_{1-x-y1}N$ where $0 \leq x1 \leq 1$, $0 \leq y1 \leq 1$, and the $In_{x1}Al_{y1}Ga_{1-x1-y1}N$ has a bandgap $E_{g1}$;
the second region of the associated sample includes p-type $In_{x2}Al_{y2}Ga_{1-x2-y2}N$ where $0 \leq x2 \leq 1$, $0 \leq y2 \leq 1$, and the $In_{x2}Al_{y2}Ga_{1-x2-y2}N$ has a bandgap $E_{g2}$; and
the quantum well of the associated sample includes an $In_{x3}Al_{y3}Ga_{1-x3-y3}N$ layer where $0 \leq x3 \leq 1$, $0 \leq y3 \leq 1$, and the $In_{x3}Al_{y3}Ga_{1-x3-y3}N$ has a bandgap $E_{g3}$ which is less than $E_{g1}$ and $E_{g2}$.

7. The apparatus as set forth in claim 6, wherein:
the first region has x1=0 and y1=0;
the second region has x2=0 and y2=0;
the first laser has a wavelength of less than or approximately 365 nm;
the second laser has a wavelength of less than or approximately 365 nm; and
the quantum well has y3=0.

8. An apparatus for evaluating a semiconductor sample, said sample having a first electrically distinct region with a bandgap $E_{g1}$ and a second electrically distinct region with a bandgap $E_{g2}$, and having a junction region disposed therebetween, the evaluation apparatus comprising:
a first laser having a wavelength tuned to photogenerate carriers in the first electrically distinct region;
a second laser disposed on the opposite side of the sample with respect to the first laser and having a wavelength tuned to photogenerate carriers in the second electrically distinct region, at least one of the first laser and the second laser producing light with a wavelength below at least $E_{g1}$ and $E_{g2}$;
an electrical biasing means for impressing an electrical field whereby at least some of the photoexcited carriers are influenced to drift toward the junction region; and
an optical detector whereby luminescence generated by recombination of the photoexcited carriers in the junction region is detected.

9. A method for characterizing a semiconductor sample, said sample having a first electrically distinct region and a second electrically distinct region, and having a junction region disposed therebetween, the characterization method comprising the steps of:
optically generating carriers in the first electrically distinct region;
forward biasing the semiconductor sample to generate drift field in the first region that effectuates a drifting of the optically generated carriers in the first electrically distinct region toward the junction region; and
measuring the optical radiation generated by radiative recombination of the optically generated carriers in the junction region.

10. The characterization method according to claim 9, further comprising the steps of:
optically generating carriers in the second electrically distinct region;
wherein the forward biasing additionally generates a drift field in the second region that effectuates a drifting of the optically generated carriers in the second electrically distinct region toward the junction region.

11. The characterization method according to claim 10, wherein the forward biasing includes:
applying a voltage between an electric contact that electrically contacts the first electrically distinct region and an electric contact that electrically contacts the second electrically distinct region so as to simultaneously generate the drift field in the first region and the drift field in the second region.

12. A characterization method for characterizing a semiconductor sample, said sample having a first electrically distinct region and a second electrically distinct region, and having a junction region disposed therebetween, the characterization method comprising:
optically generating carriers in the first electrically distinct region;
generating an externally applied drift field described by a field vector E in the first region that effectuates a drifting of the optically generated carriers in the first electrically distinct region toward the junction region; and
measuring the optical radiation generated by radiative recombination of the optically generated carriers in the junction region;
wherein the step of optically generating carriers in the first electrically distinct region includes optically generating carriers substantially within a distance $d=\mu\tau|E|$ of the junction region, where $\mu$ is the drift mobility of the optically generated carriers in the first material, and $\tau$ is the lifetime of the optically generated earners in the first material, whereby the fraction of the optically generated carriers that enter the junction region is approximately 1/e.

13. A characterization method for characterizing a semiconductor sample, said sample having a first electrically distinct region and a second electrically distinct region, and having a junction region disposed therebetween, the characterization method comprising the steps of:

optically generating carriers in the first electrically distinct region;

generating an externally applied drift field in the first region that effectuates a drifting of the optically generated carriers in the first electrically distinct region toward the junction region;

measuring the optical radiation generated by radiative recombination of the optically generated carriers in the junction region;

estimating quantitatively the volume recombination rate in the junction region based on the step of measuring the optical radiation generated by radiative recombination of the optically generated carriers in the junction region;

estimating quantitatively the volume density of optically generated carriers in the first electrically distinct region; and estimating quantitatively the electroluminescence efficiency based upon the volume recombination rate and the volume density of optically generated carriers.

14. A characterization method for characterizing a semiconductor sample, said sample having a first electrically distinct region and a second electrically distinct region, and having a junction region disposed therebetween, the characterization method comprising:

optically generating carriers in the first electrically distinct region;

generating an externally applied drift field in the first region that effectuates a drifting of the optically generated carriers in the first electrically distinct region toward the junction region, the drift field effectuating electrical carrier generation that is negligible compared to the optical carrier generation; and measuring the optical radiation generated by radiative recombination of the optically generated carriers in the junction region.

15. A method for characterizing a light emitting diode (LED) structure sample, said sample having an n-type region and a p-type region, and having a junction region disposed therebetween, the characterization method comprising the steps of:

optically generating carriers in the n-type region by light impingement thereon;

optically generating carriers in the p-type region by light impingement thereon;

electrically biasing the junction to effectuate a drifting of the optically generated carriers toward the junction region;

optically chopping the impinging light with an optical chopper;

detecting the optical radiation with an optical detector; and measuring the optical detector signal at the optical chopping frequency using a lock-in amplifier that is in operative communication with the optical chopper and the optical detector.

16. A characterization method for characterizing a light emitting diode (LED) structure sample, said sample having an n-type region and a p-type region, and having a junction region disposed therebetween, the characterization method comprising the steps of:

optically generating carriers in the n-type region by light impingement thereon;

optically generating carriers in the p-type region by light impingement thereon;

measuring the optical radiation generated by radiative recombination of the optically generated carriers in the junction region;

repeating the generating, biasing, and measuring steps at a plurality of wavelengths of the at least one optical source; and estimating transport properties of the at least one region therefrom.

17. A characterization method for characterizing a light emitting diode (LED) structure sample, said sample having an n-type region and a p-type region, and having a junction region disposed therebetween, the characterization method comprising the steps of:

optically generating carriers in the n-type region by light impingement thereon;

optically generating carriers in the p-type region by light impingement thereon;

measuring the optical radiation generated by radiative recombination of the optically generated carriers in the junction region;

repeating the generating, biasing, and measuring steps at a plurality of intensities of the at least one optical source; and estimating the effects of high injection levels from the measuring.

* * * * *